United States Patent [19]

Kiso et al.

[11] Patent Number: 5,360,921

[45] Date of Patent: Nov. 1, 1994

[54] PROCESS FOR PREPARING CYCLOPENTADIENYL GROUP-CONTAINING SILICON COMPOUND OR CYCLOPENTADIENYL GROUP-CONTAINING GERMANIUM COMPOUND

[75] Inventors: Yoshihisa Kiso; Koji Kawaai; Masatoshi Nitabaru, all of Kuga, Japan

[73] Assignee: Mitsui Petrochemical Industries, Ltd., Tokyo, Japan

[21] Appl. No.: 208,590

[22] Filed: Mar. 11, 1994

[30] Foreign Application Priority Data

Mar. 22, 1993 [JP] Japan .................. 5-062216

[51] Int. Cl.$^5$ ............................ C07F 7/08; C07F 7/30
[52] U.S. Cl. ........................................ 556/478; 556/95
[58] Field of Search ................... 556/478, 95

[56] References Cited

U.S. PATENT DOCUMENTS

| | | | |
|---|---|---|---|
| 2,974,157 | 3/1961 | Jex | 556/478 |
| 4,640,968 | 2/1987 | Watanabe et al. | 556/478 X |
| 4,650,891 | 3/1987 | Lennon . | |
| 4,672,135 | 6/1987 | Lennon . | |
| 4,985,576 | 1/1991 | Rohrmann et al. . | |
| 5,068,386 | 11/1991 | Shirahata . | |
| 5,118,829 | 6/1992 | Gohndrone | 556/478 X |
| 5,239,022 | 8/1993 | Winter et al. . | |
| 5,243,001 | 9/1993 | Winter et al. . | |

FOREIGN PATENT DOCUMENTS

| | | |
|---|---|---|
| 2017190 | 11/1990 | Canada . |
| 2076775 | 2/1993 | Canada . |
| 2080576 | 4/1993 | Canada . |
| 2084015 | 5/1993 | Canada . |
| 2084017 | 5/1993 | Canada . |
| 0129368 | 12/1984 | European Pat. Off. . |
| 0574597 | 12/1993 | European Pat. Off. . |
| 0576970 | 1/1994 | European Pat. Off. . |

OTHER PUBLICATIONS

"Zirconocene-$\eta^4$-1,3-Pentadiene Complex and Its Higher Homologues." Organometallics 1984, 3, pp. 1470–1478, 1984 American Chemical Society, Yasuda et al.

"Metallkomplexe mit verbruckten permethylierten Cyclopentadienylliganden", VCH Verlagsgesellschaft mbH D-6940 Weinheim, 1986, pp. 1750–1754.

Manipulation of Organolanthanide Coordinative Unsaturation, Synthesis, Structures, Structural Dynamics, Comparative Reactivity, and Comparative Thermochemistry of Dinuclear $\mu$-Hydrides and $\mu$-Alkyls with [$\mu$-R$_2$Si(Me$_4$C$_5$) (C$_5$H$_4$)]$_2$ Supporting Ligation, J. Am. Chem. Soc. 1990, 112, 9558–9575.

*Primary Examiner*—Paul F. Shaver
*Attorney, Agent, or Firm*—Birch, Stewart, Kolasch & Birch

[57] ABSTRACT

Disclosed is a process for preparing a cyclopentadienyl group-containing silicon compound or a cyclopentadienyl group-containing germanium compound, comprising reacting (i) a lithium, sodium or potassium salt of a cyclopentadiene derivative with (ii) a silicon halide compound or a germanium halide compound in the presence of a cyanide or a thiocyanate. The cyanide or the thiocyanate is preferably a copper salt. According to the process of the invention, a cyclopentadienyl group-containing silicon compound or a cyclopentadienyl group-containing germanium compound, which is very useful for the preparation of a metallocene complex catalyst component, can be prepared in a high yield for a short period of time.

4 Claims, No Drawings

PROCESS FOR PREPARING CYCLOPENTADIENYL GROUP-CONTAINING SILICON COMPOUND OR CYCLOPENTADIENYL GROUP-CONTAINING GERMANIUM COMPOUND

FIELD OF THE INVENTION

The present invention relates to a process for preparing a cyclopentadienyl group-containing silicon compound or a cyclopentadienyl group-containing germanium compound.

BACKGROUND OF THE INVENTION

A metallocene complex catalyst containing a cyclopentadienyl group as a ligand has been paid much attention in recent years as a novel catalyst for olefin polymerization. Of such cyclopentadienyl group ligands, a cyclopentadienyl group-containing silicon compound and a cyclopentadienyl group-containing germanium compound have been particularly paid attention because they are able to form a chiral and stereorigid metallocene complex when they coordinate to a central metal (e.g., zirconium). Especially, a zirconocene complex having such ligand is known as an important catalyst component capable of producing an olefin polymer with a high polymerization activity, as described in European Patent Application No. 129,368.

Further, the metallocene complex having such ligand is also useful as a catalyst for a Dieis-Alder react ion or a hydrogenation reaction.

The cyclopentadienyl group-containing silicon compound (or cyclopentadienyl group-containing germanium compound) employable as a ligand of the metallocene complex is generally prepared by causing a lithium, sodium or potassium salt of cyclopentadiene derivative to react with a silicon halide compound (or a germanium halide compound), as described in "Organometallics" 3 1470 (1984), "Chem. Berichte" 119 1750 (1986), "J. Am. Chem. Soc." 112 9558 (1990), Japanese Patent Laid-Open Publications No. 1285/1990, No. 21607/1991, No. 268307/1992 and No. 8308/1992, EP 0549900A1, EP 0545303A1, EP 0537686A1, EP 30647A1, EP 0574597A1 and EP 0576970A1.

In detail, in Japanese Patent Laid-Open Publication No. 221285/1990 for example, a solution of an indenyl lithium salt prepared from indene and n-butyllithium is slowly added to a dimethyldichlorosilane solution, and they are reacted with each other overnight to obtain dimethyldi(1-indenyl)silane in a 71% yield. In Japanese Patent Laid-Open Publication No. 268307/1992, dimethyldi (2-methyl-1-indenyl) silane is obtained in a 16% yield in a manner similar to the above.

In "Chem. Berichte" 119 1750 (1986), a solution containing 1,2,3,4-tetramethylcyclopentadienyl lithium and dimethyldichlorosilane is heated for 5 days to obtain dimethylbis(2,3,4,5-tetramethylcyclopentadienyl)-silane in a 65% yield.

In any of the conventional processes as described above, however, the reaction must be carried out for a long period of time and the yield is low. Especially in the case of preparing a compound having such a structure that two or more groups of large steric hindrance are bonded to silicon or germanium, the yield of the compound is further lowered.

Accordingly, the advent of a process for preparing a cyclopentadienyl group-containing silicon compound or a cyclopentadienyl group-containing germanium compound in a high yield for a short period of time will be of industrially great value, because a metallocene complex catalyst component or the like can be prepared with high productivity.

OBJECT OF THE INVENTION

It is, therefore, an object of the present invention to provide a process for preparing a cyclopentadienyl group-containing silicon compound or a cyclopentadienyl group-containing germanium compound, said compound being useful for the preparation of a metallocene complex catalyst component or the like, in a high yield for a short period of time.

SUMMARY OF THE INVENTION

The process for preparing a cyclopentadienyl group-containing silicon compound or a cyclopentadienyl group-containing germanium compound according to the present invention comprises reacting:

(i) a lithium, sodium or potassium salt of a cyclopentadiene derivative, with (ii) a silicon halide compound or a germanium halide compound, in the presence of a cyanide or a thiocyanate.

In the present invention, the cyanide (a compound containing at least one cyano group) or the thiocyanate (a compound containing at least one thiocyano group) is preferably a copper salt.

The metallic salt of cyclopentadiene derivative (i) used for the invention is preferably a lithium salt of a cyclopentadiene derivative.

The silicon halide compound (ii) is preferably dihalodialkylsilane, dihalodiarylsilane or dihaloalkylarylsilane; and the germanium halide compound (ii) is preferably dihalodialkylgermane, dihalodiarylgermane or dihaloalkylarylgermane.

DETAILED DESCRIPTION OF THE INVENTION

The process for preparing a cyclopentadienyl group-containing silicon compound or a cyclopentadienyl group-containing germanium compound according to the present invention will be described in detail hereinafter.

In the process for preparing a cyclopentadienyl group-containing silicon compound or a cyclopentadienyl group-containing germanium compound according to the invention, (i) a lithium, sodium or potassium salt of a cyclopentadiene derivative is reacted with (ii) a silicon halide compound or a germanium halide compound in the presence of a cyanide or a thiocyanate.

(i) Metallic Salt of Cyclopentadiene Derivative

Examples of the cyclopentadiene derivative for forming the lithium, sodium or potassium salt of cyclopentadiene derivative (i) (hereinafter sometimes referred to as "metallic salt of cyclopentadiene derivative (i)") used in the above reaction include cyclopentadiene and cyclopentadiene compounds having a substituent group. Examples of the substituent group include a hydrocarbon group of 1 to 30 carbon atoms; an alkoxy group such as methoxy, ethoxy and butoxy; an aryloxy group such as phenoxy, methylphenoxy and dimethylphenoxy; a nitro group; an amino group such as amino, dimethylamino and diethylamino; an urea group such as urea, N',N'-dimethylurea and N,N',N'-trimethylurea; halogen such as F, Cl, Br and I; an organosilicon group such as trimethylsilyl, triethylsilyl, tributylsilyl and triphenylsilyl; an organogermanium group such as trimethylgermyl, triethylgermyl, tributylgermyl and triphenylgermyl; and an organotin group such as trimethylstannyl, triethylstannyl, tributylstannyl and triphenylstannyl. The cyclopentadiene compound may have plural substituent groups, and the plural substituent groups may be the same or different from each other.

Of the above substituent groups, examples of the hydrocarbon group of 1 to 30 carbon atoms include an alkyl group such as methyl, ethyl, propyl, butyl, hexyl, cyclohexyl, octyl, decyl and dodecyl; and an aryl group such as phenyl, methylphenyl, dimethylphenyl, octylphenyl, naphthyl, phenanthryl and anthryl. These groups may be bonded to carbon adjacent to cyclopentadiene to form a ring. Examples of the ring include an indene derivative, a 4,5,6,7-tetrahydroindene derivative, a benzoindene derivative, an acenaphthindene derivate and a fluorene derivative. The above substituent groups may be further substituted with an alkoxy group such as methoxy, ethoxy and butoxy; an aryloxy group such as phenoxy, methylphenoxy and dimethylphenoxy; a nitro group; an amino group such as amino, dimethylamino and diethylamino; an urea group such as urea, N',N'-dimethylurea and N,N',N'-trimethylurea; halogen such as F, Cl, Br and I; an organosilicon group such as trimethylsilyl, triethylsilyl, tributylsilyl and triphenylsilyl; an organogermanium group such as trimethylgermyl, triethylgermyl, tributylgermyl and triphenylgermyl; and an organot in group such as trimethylstannyl, triethylstannyl, tributylstannyl and triphenylstannyl. Listed below are examples of the cyclopentadiene derivative, but the cyclopentadiene derivative employable for the invention is in no way limited to those examples.

Cyclopentadiene,
Methylcyclopentadiene,
1,2-Dimethylcyclopentadiene,
1,2,3- or 1,2,4-Trimethylcyclopentadiene,
1,2,3,4-Tetramethylcyclopentadiene,
tert-Butylcyclopentadiene,
Ethylcyclopentadiene,
Phenylcyclopentadiene,
Trimethylsilylcyclopentadiene,
1,2-Dimethyl-4-ethylcyclopentadiene,
1,2-Dimethyl-4-tert-butylcyclopentadiene,
1,2-Dimethyl-4-trimethylsilylcyclopentadiene,
Naphthylcyclopentadiene,
1,2-Dimethyl-4-(3-methoxypropyl)cyclopentadiene,
Indene,
1-Methylindene,
2-Methylindene,
2-Ethylindene,
2-Isopropylindene,
2-Phenylindene,
2-Trimethylsilylindene,
3-Methylindene,
1 or 3-tert-butylindene,
4-Methylindene,
5-Methyl indene,
6-Methyl indene,
7-Methylindene,
2-Methyl-4-methoxyindene,
4,7-Dimethylindene,
2,4-Dimethylindene,
2,4,7-Trimethylindene,
2,4-Diisopropylindene,
2-Methyl-4-phenyl indene,
2-Methyl-4-α-naphthyl indene,
2-Methyl-4,6-diisopropylindene,
2,4,6-Trimethylindene,
2-Methyl-4-ethyl indene,
2-Methyl-4-tert-butyl indene
2-Ethyl-4-methyl indene,
2-Methyl-4,5-benzoindene,
2-Methyl-α-acenaphthindene,
2-Methyl-4-isopropylindene,
4,5,6,7-Tetrahydroindene,
2-Methyl-4,5,6,7-tetrahydroindene, and
Fluorene.

In the invention, preferably used are cyclopentadiene having 2 to 4 substituent groups, particularly 3 or 4 substituent groups, 4,5,6,7-tetrahydroindene derivatives, indene derivatives and fluorene derivatives. For example, 1,2,4-trimethylcyclopentadiene, 1,2,3,4-tetramethylcyclopentadiene, 1,2-dimethyl-4-tert-butylcyclopenadiene, 1,2-dimethyl-4-trimethylsilylcyclopentadiene, 1,2-dimethyl-4-ethylcyclopentadiene, indene, 2-methylindene, 2-ethylindene, 4,5,6,7-tetrahydroindene, 2-methyl-4,5,6,7-tetrahydroindene and fluorene are preferred.

In the present invention, lithium, sodium or potassium salts of the above cyclopentadiene derivatives are used. Of these, preferred are lithium salts of the cyclopentadiene derivatives.

The lithium, sodium or potassium salt of cyclopentadiene derivative (i) for the use in the invention can be synthesized by reacting the cyclopentadiene derivative with metallic lithium, metallic sodium or metallic potassium (or compounds of these metals) in an inert solvent such as diethyl ether, tetrahydrofuran, hexane or benzene.

Examples of the compound of lithium, sodium or potassium include hydrides, amidation products, alkylation products and arylation products, of those metals.

(ii) Silicon Halide Compound or Germanium Halide Compound

Examples of halogen for forming the silicon halide compound or the germanium halide compound used for the invention include fluorine, chlorine, bromine and iodine. Of these, preferred are chlorine and bromine, and more preferred is chlorine. The silicon halide compound or the germanium halide compound has 1 to 4 halogen atoms, and these halogens may be the same or different from each other. Examples of the substituent groups of the silicon halide compound or the germanium halide compound, other than halogens, include hydrogen; a hydrocarbon group of 1 to 30 carbon atoms; an organosilicon group such as trimethylsilyl, triethylsilyl, triphenylsilyl and methyldiphenylsilyl; an organogermaninum group such as trimethylgermyl, triethylgermyl, triphenylgermyl and methyldiphenylgermyl; an alkoxy group such as methoxy and ethoxy; and an aryloxy group such as phenoxy and methylphenoxy. When the silicon halide compound or the germanium halide compound has plural substituent groups, the plural substituent groups may be the same or different from each other.

Examples of the above hydrocarbon group of 1 to 30 carbon atoms include an alkyl group such as methyl, ethyl, butyl, hexyl, octyl, dodecyl and cyclohexyl; and an aryl group such as phenyl, tolyl, dimethylphenyl and naphthyl. These hydrocarbons may be further substituted with, for example, an alkoxy group such as methoxy and ethoxy; an aryloxy group such as phenoxy and methylphenoxy; a nitro group; an amino group such as amino, dimethylamino and diethylamino; an urea group such as urea, N',N'-dimethylurea and N,N',N'-trimethylurea; halogen such as F, Cl, Br and I; an organosilicon group such as trimethylsilyl, triethylsilyl and tributylsilyl; an organogermanium group such as trimethylgermyl, triethylgermyl and tributylgermyl; and an organotin group such as trimethylstannyl, triethylstannyl and tributylstannyl.

Listed below are examples of the silicon halide compound, but the silicon halide compound employable for the invention is in no way limited to those examples.

Silicon monohalide compounds, such as:
Methylchlorosilane,
Dimethylchlorosilane,
Diphenylchlorosilane,
Trimethylchlorosilane,
Triethylchlorosilane,
Triphenylchlorosilane,
Methyldiphenylchlorosilane,
Methylphenylbromosilane, and
Methylphenyliodosilane;

Silicon dihalide compounds (dihalosilane compounds), such as:
Methyldichlorosilane,
Phenyldichlorosilane,
Dimethyldichlorosilane,
Diethyldichlorosilane,
Di-tert-butyldichlorosilane,
Diphenyldichlorosilane,
Di(2-methylphenyl)dichlorosilane,
Di(2,6-dimethylphenyl) dichlorosilane,
Methylphenyldichlorosilane,
Dicyclohexyldichlorosilane,
1,3-Trimethylenedichlorosilane,
1,4-Tetramethylenedichlorosilane,
1,5-Pentamethylenedichlorosilane,
Di(trimethylsilyl)dichlorosilane,
Methyltrimethylsilyldichlorosilane,
Dinaphthyldichlorosilane,
Methylnaphthyldichlorosilane,
1,1,2,2-Tetramethyl-1,2-dichlorodisilane, and
Dimethyldibromosilane; and Silicon trihalide compounds, such as:
Trichlorosilane,
Methyltrichlorosilane,
Phenyltrichlorosilane, and
Phenyltribromosilane; and Silicon tetrahalide compounds, such as:
Tetrachlorosilane.

Examples of the germanium halide compound include compounds wherein the silicon is replaced with germanium in the above examples of the silicon halide compound.

Of the above examples, preferred are compounds in which a secondary or tertiary alkyl group or an aromatic hydrocarbon group, specifically, an isopropyl group, a sec-butyl group, a cyclohexyl group, a tert-butyl group, a phenyl group, a tolyl group, a dimethylphenyl group, a naphthyl group, etc. is bonded to silicon or germanium atom. Also preferred are silicon dihalide compounds having these groups or germanium dihalide compounds having these groups. Of these, particularly preferred are dihalodialkylsilane, dihalodiarylsilane and dihaloalkylarylsilane. Likewise, particularly preferred are dihalodialkylgermane, dihalodiarylgermane and dihaloalkylarylgermane.

Process for Preparing Cyclopentadienyl Group-Containing Silicon or Germanium Compound In the present invention, the metallic salt of cyclopentadiene derivative (i) and the silicon halide compound or germanium halide compound (ii) are reacted with each other in the presence of a cyanide (a compound containing at least one cyano group) or a thiocyanate (a compound containing at least one thiocyano group).

Examples of the cyano compound employable in the invention include:
HCN, LiCN, NaCN, KCN, CsCN, Ca(CN)$_2$, Mg(CN)$_2$, Ba(CN)$_2$, Sr(CN)$_2$, BrCN, ICN, P(CN)$_3$, P(CN)$_5$, Al(C$_2$H$_5$)CN, Cd(CN)$_2$, Hg(CN)$_2$, Mn(CN)$_2$, Mo(CN)$_4$, V(CN)$_4$, CuCN, Cu(CN)$_2$, AgCN, AuCN, Au(CN)$_3$, Zn(CN)$_2$, PbCN, Co(CN)$_2$, Pd(CN)$_2$, Pt(CN)$_2$, K$_2$Pt(CN)$_6$, Ru(CN)$_2$, Os(CN)$_2$ and Rh(CN)$_4$;

ammonium cyanides, such as NH$_4$CN, (C$_2$H$_5$)$_4$NCN and (C$_4$H$_9$)$_4$NCN;

compounds having cyano ion, such as (C$_4$H$_9$)$_3$SnCN, (CH$_3$)$_3$SiCN and (CH$_3$)$_3$GeCN; and cyano group-containing anion exchange resins.

Also employable are compounds capable of producing cyano ion in the reaction solution.

Examples of the thiocyanate include compounds wherein the (—CN) group is replaced with a (—SCN) group in the above examples of the cyano compound.

Of the above examples, a copper salt of the cyanide or a copper salt of the thiocyanate is particularly preferably used in the invent ion .

According to the process of the present invention, a bis(cyclopentadienyl)silicon compound is prepared by reacting, for example, (i) a lithium salt of a cyclopentadiene derivative with (ii) a silicon halide compound in the presence of copper cyanide. The reaction formula in this case is described below.

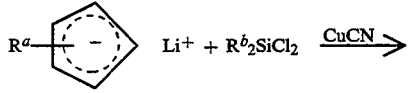

Lithium salt of cyclopentadiene derivatives

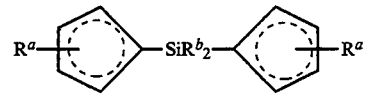

In the above reaction, the metallic salt of cyclopentadiene derivative (i) and the silicon halide compound or germanium halide compound (ii) are used in a molar ratio [(i):(ii)] of usually 1:20 to 20:1, preferably 1:5 to 5:1, more preferably 3:1 to 2:1.

The cyanide (or the thiocyanate) is used in such an amount that a molar ratio of the cyanide (or the thiocyanate) to the silicon halide compound or germanium halide compound (ii) is in the range of 1:1 to 1:100,000, preferably 1:10 to 1:1,000.

The reaction is generally carried out in the presence of a solvent.

Examples of the reaction solvent include:
hydrocarbons, such as pentane, hexane, heptane, octane, cyclohexane, petroleum ether, benzene and toluene;

ether compounds, such as diethyl ether, dimethoxyethane, tetraglyme, diisopropyl ether, tetrahydrofuran, diphenyl ether, tert-butyl methyl ether, dioxane and anisole;

amide compounds, such as 1-methyl-2-pyrrolidone;

urea compounds, such as tetramethylurea and 1,3-dimethyl-2-imidazolidone; and sulfone compounds, such as sulfolane.

Of these, preferred are ether compounds.

The reaction may be carried out either batchwise or continuously.

The cyanide or the thiocyanate may be beforehand added to a solution of the metallic salt of cyclopentadiene derivative (i) or to a solution of the silicon halide compound or germanium halide compound (ii). Otherwise, it is also possible that the metallic salt (i) is mixed with the compound (ii) and then to the resulting mixture is added the cyanide or the thiocyanate.

The reaction between the metallic salt of cyclopentadiene derivative (i) and the silicon halide compound or germanium halide compound (ii) is carried out at a temperature of −80° to 200° C., preferably −50° to 100° C., more preferably −30° to 80° C.

The reaction time is in the range of usually 1 minute to 2 weeks, preferably 10 minutes to 1 week, more preferably 30 minutes to 4 days.

In the present invention, to the above-mentioned reaction system may be added a diamine compound such as tetramethylethylenediamine or a phosphoric amide compound such as hexamethylphosphoric triamide, if necessary.

In the process for preparing a cyclopentadienyl group-containing silicon compound or a cyclopentadienyl group-containing germanium compound according to the present invention, a silicon polyhalide compound (or a germanium polyhalide compound) can be used as the silicon halide compound (or germanium halide compound) (ii), to obtain a cyclopentadienyl group-containing silicon compound (or germanium compound) in which all the halogens of the silicon polyhalide compound (or germanium polyhalide compound) have been substituted with cyclopentadienyl groups, or to obtain a cyclopentadienyl group-containing silicon compound (or germanium compound) in which some of the halogens of the silicon polyhalide compound (or germanium polyhalide compound) have been substituted with cyclopentadienyl groups.

As in the latter case, in the preparation of a cyclopentadienyl group-containing silicon compound (or germanium compound) in which some of the halogens of the silicon polyhalide compound (or germanium polyhalide compound) (ii) have been substituted with cyclopentadienyl groups, the silicon polyhalide compound (or germanium polyhalide compound) (ii) is used in such an amount that a molar ratio, in terms of one halogen atom to be substituted, between the compound (ii) and the metallic salt of cyclopentadiene derivative (i) is in the range of 1:2 to 2:1, preferably 1:1.2 to 1.2:1.

Of the aforesaid adding methods, preferably used in the above case is a method of dropwise adding the metallic salt of cyclopentadiene derivative (i) or its solution to the silicon polyhalide compound or germanium polyhalide compound (ii) or its solution.

According to the process of the present invention as described above, a cyclopentadienyl group-containing silicon compound or a cyclopentadienyl group-containing germanium compound can be prepared in a high yield for a short period of time.

Even in the preparation of a cyclopentadienyl group-containing silicon compound or a cyclopentadienyl group-containing germanium compound each having a functional group of large steric hindrance, the compound can be obtained in a high yield for a short period of time. More specifically, as described above with respect to each starting materials, when the metallic salt of cyclopentadiene derivative (i) is a metallic salt of cyclopentadienyl group having 2 to 4 substituent groups, particularly 3 or 4 substituent groups, and/or when the silicon halide compound (or germanium halide compound) (ii) has a secondary or tertiary carbon or an aromatic carbon, the effect given by coexistence of the cyanide or the thiocyanate is increased.

Cyclopentadienyl Group-Containing Silicon Compound or Cyclopentadienyl Group-Containing Germanium Compound Examples of the cyclopentadienyl group-containing silicon compound prepared by the process of the invention include silane compound having monocyclopentadienyl derivative substituent, silane compound having dicyclopentadienyl derivative substituent, silane compound having tricyclopentadienyl derivative substituent and silane compound tetracyclopentadienyl derivative substitutent. Examples of the cyclopentadienyl group-containing germanium compound include compounds wherein the silicon atom is replaced with germanium in the above examples.

Examples of the cyclopentadienyl derivative include cyclopentadiene and cyclopentadiene compounds having a substituent group. Examples of the substituent group include a hydrocarbon group of 1 to 30 carbon atoms, an alkoxy group, an aryloxy group, an amino group, halogen, an organosilicon group, an organogermanium group and an organotin group. The cyclopentadiene compounds may have plural substituent groups, and the plural substituent groups may be the same or different from each other.

Of the above substituent groups, examples of the hydrocarbon group of 1 to 30 carbon atoms include an alkyl group, an aryl group and an alkylaryl group, and they may be bonded carbon adjacent to cyclopentadiene to form a ring. These substituent groups may be further substituted with an alkoxy group, an aryloxy group, a nitro group, an amino group, an urea group, halogen, an organosilicon group, an organogermanium group and an organotin group.

As other substituent group than the cyclopentadienyl derivative among the substituent groups of the cyclopentadienyl group-containing silicon compound or the cyclopentadienyl group-containing germanium compound, there can be mentioned hydrogen, a hydrocarbon group of 1 to 30 carbon atoms, an alkoxy group, an aryloxy group, halogen, an organosilicon group and an organogermanium group. These substituent groups may be the same or different from each other. Examples of the hydrocarbon group of 1 to 30 carbon atoms include an alkyl group and an aryl group, and they may be further substituted with an alkoxy group, an allyloxy group, a nitro group, an amino group, an urea group, halogen, an organosilicon group, an organogermanium group, an organotin group, an organophosphorus group and an organoaluminum group.

Listed below are examples of the cyclopentadienyl group-containing silicon compound, but the cyclopentadienyl group-containing silicon compound prepared by the process of the invention is in no way limited to those examples.

Monocyclopentadienyl silicon compounds, such as:
Cyclopentadienyltrimethylsilane,
Cyclopentadienyltriphenylsilane,
Cyclopentadienyltriisopropylsilane,
Cyclopentadienylmethyldiphenylsilane
2-Methylcyclopentadienyltriphenylsilane,
2,3,4-Trimethylcyclopentadienyltrimethylsilane,
2,3,4,5-Tetramethylcyclopentadienyltrimethylsilane,
2,3,4,5-Tetramethylcyclopentadienyldimethylchlorosilane,
2,3,4,5-Tetramethylcyclopentadienyldiphenylchlorosilane,
2,3,4,5-Tetramethylcyclopentadienylmethyldichlorosilane
1-Indenyltrimethylsilane,
1-Indenyltriphenylsilane,
2-Methyl-1-indenyltriphenylsilane,
2-Methyl-1-indenyldiphenylchlorosilane,
2-Methyl-1-indenylphenyldichlorosilane, and
2-Methyl-4-isopropyl-1-indenyldiphenylchlorosilane;
Di(cyclopentadienyl)silicon compounds, such as:
Di(cyclopentadienyl)dimethylsilane,
Di(cyclopentadienyl)phenylmethylsilane,
Di(cyclopentadienyl)diphenylsilane,
Di(2,3,5-trimethylcyclopentadienyl)methylsilane,
Di(2,3,5-trimethylcyclopentadienyl)dimethylsilane,
Di(2,3,5-trimethylcyclopentadienyl)phenylmethylsilane,
Di(2,3,5-trimethylcyclopentadienyl) diphenylsilane,
Di(2,3,5-trimethylcyclopentadienyl)diisopropylsilane,
Di(2,3,5-trimethylcyclopentadienyl)t-butylmethylsilane,
Di(1-indenyl)methylsilane,
Di(1-indenyl)dimethylsilane,
Di(1-indenyl)phenylmethylsilane,
Di(1-indenyl)diphenylsilane,
Di(1-indenyl)ditolylsilane,
Di(1-indenyl)dinaphthylsilane,
Di(1-indenyl)di(2,6-dimethylphenyl)silane,
Di(1-indenyl)phenylchlorosilane,
Di(1-indenyl)dichlorosilane,
Di(2-methyl-1-indenyl)methylsilane,
Di(2-methyl-1-indenyl)dimethylsilane,
Di(2-methyl-1-indenyl)diphenylsilane,
Di(2-methyl-1-indenyl)dichlorosilane,
Di(2-methyl-1-indenyl)chloromethylsilane,
Di(2-phenyl-1-indenyl)dimethylsilane,
Di(2-methyl-4-trimethylsilyl-1-indenyl)dimethylsilane,
Di(2-methyl-4-phenyl-1-indenyl )dimethylsilane,
Di(2-methyl-4-tert-butyl-1-indenyl)dimethylsilane,
Di(2-ethyl-4-methyl-1-indenyl)dimethylsilane,
Di(2-methyl-4,5-benzo-1-indenyl)dimethylsilane,
Di(2-methyl-α-acenaphth-1-indenyl )dimethyls ilane,
Di(2-methyl-α-naphthyl-1-indenyl)dimethylsilane,
Di(2-methyl-4,6-disopropyl-1-indenyl)dimethylsilane,
Di(2,4,6-trimethyl-1-indenyl)dimethylsilane,
2-Methyl-1-indenyl-cyclopentadienyldimethylsilane, and
1-Fluorenyl-cyclopentadienyldimethylsilane;
Tri(cyclopentadienyl)silicon compounds, such as:
Tri(cyclopentadienyl)silane,
Tri(cyclopentadienyl)methylsilane,
Tri(cyclopentadienyl)phenylsilane,
Tri(cyclopentadienyl)isopropylsilane,
Tri(cyclopentadienyl)-t-butylsilane,
Tri(cyclopentadienyl)chlorosilane,
Tri(1-indenyl)silane,
Tri(1-indenyl)chlorosilane, and
Tri(1-indenyl)phenylsilane; and
Tetra(cyclopentadienyl)silicon compounds, such as:
Tetra(cyclopentadienyl)silane, and
Tetra(3-methylcyclopentadienyl)silane.

Examples of the cyclopentadienyl group-containing germanium compound prepared by the process of the present invention include compounds wherein the silicon is replaced with germanium in the above examples of the cyclopentadienyl group-containing silicon compound.

As described before, a metallocene complex can be obtained by reacting the cyclopentadienyl group-containing silicon compound or the cyclopentadienyl group-containing germanium compound prepared by the process of the invention with a compound of transition metal such as zirconium. This metallocene complex is used as a highly active catalyst component for olefin polymerization. When the cyclopentadienyl group-containing silicon compound or the cyclopentadienyl group-containing germanium compound is used to form a ligand of the metallocene compound, preferably used as the compound are those containing cyclopentadiene derivative groups such as a cyclopentadienyl group having 2 to 4 substituent groups, an indenyl group and a fluorenyl group. More preferred are compounds containing cyclopentadiene derivative groups such as a cyclopentadienyl group having 3 or 4 substituent groups, a 1-position-substituted indenyl group, a 2-position-substituted indenyl group, a 3-position-substituted indenyl group, a 1- and 2-positions-substituted indenyl group, a 1- and 3-positions-substituted indenyl group, a 2- and 3-positions-substituted indenyl group, and a fluorenyl group.

EFFECT OF THE INVENTION

According to the process of the present invention, a cyclopentadienyl group-containing silicon compound or a cyclopentadienyl group-containing germanium compound can be prepared in a high yield for a short period of time.

Particularly, even in the preparation of a cyclopentadienyl group-containing silicon compound in which at least two groups of large steric hindrance are bonded to silicon or in the preparation of the cyclopentadienyl group-containing germanium compound in which at least two groups of large steric hindrance are bonded to germanium, the compound can be obtained in a high yield for a short period of time.

EXAMPLE

The present invention will be further described below with reference to examples, but it should be construed that the invention is in no way limited to those examples.

EXAMPLE 1

All the reactions were carried out in a nitrogen atmosphere.

Indene (8.4 mmol), CuCN (0.23 mmol) and 14 ml of diethyl ether were cooled to $-10°$ C. To the resulting mixture was dropwise added 6 ml of a hexane solution obtained by dissolving n-butyllithium (9.4 mmol) in 6 ml of hexane, over a period of 15 minutes, and they were reacted with each other for 1 hour at −10° C. with stirring.

The temperature of the reaction solution obtained in the above was elevated to room temperature. Then, to the solution was added diethyl ether solution obtained by dissolving phenylmethyldichlorosilane (4.6 mmol) in 5 ml of diethyl ether, over a period of 20 minutes at 20° C., and they were reacted with each other for 1 hour at room temperature with stirring.

The reaction solution was neutralized with an aqueous solution of ammonium chloride, and the resulting organic layer was extracted with diethyl ether.

Through the above reactions, di(1-indenyl) phenylmethylsilane was obtained. The di(1-indenyl)phenylmethylsilane was analyzed by means of gas chromatography. The results are set forth in Table 1 .

COMPARATIVE EXAMPLE 1

The procedures of Example 1 were repeated except for not using CuCN to obtain a reaction product. The results are set forth in Table 1.

EXAMPLES 2–4

The procedures of Example 1 were repeated except for using each of thiocyanates set forth in Table 1 in place of CuCN to obtain a reaction product. The results are set forth in Table 1.

EXAMPLE 5

All the reactions were carried out in a nitrogen atmosphere.

1,2,4-trimethylcyclopentadiene (9 mmol), CuCN (0.25 mmol)and 14 ml of tetrahydrofuran were cooled to −10° C. To the resulting mixture was dropwise added a solution obtained by dissolving n-butyllithium (9.9 mmol) in 6 ml of hexane, over a period of 15 minutes at −10° C., and they were reacted with each other for 1 hour at −10° C. with stirring.

To the reaction solution obtained in the above were dropwise added dimethyldichlorosilane (5 mmol) and 4 ml of tetrahydrofuran over a period of 15 minutes at −10° C., and they were reacted with each other for 24 hours at room temperature with stirring.

The reaction solution was neutralized with an aqueous solution of ammonium chloride, and the resulting organic layer was extracted with diethyl ether.

Through the above reactions, di(2,3,5-trimethylcyclopentadienyl)dimethylsilane was obtained in a yield. The amount of the unreacted 1,2,4-trimethylcyclopentadiene was 3%.

EXAMPLE 6

The procedures of Example 5 were repeated except for using CuSCN in place of CuCN to obtain a reaction product. The results are set forth in Table 1.

COMPARATIVE EXAMPLE 2

The procedures of Example 5 were repeated except for not using CuCN to obtain a reaction product. The results are set forth in Table 1.

TABLE 1

| | Cyanide or Thiocyanate (*A) | *A/Silicon compound [molar ratio] | Yield of Reaction product [%] | Conversion of Cyclopentadiene derivative [%] |
|---|---|---|---|---|
| Ex. 1 | CuCN | 0.05 | 62 | 94 |
| Ex. 2 | CuSCN | 0.05 | 64 | 97 |
| Ex. 3 | AgSCN | 0.05 | 40 | 81 |
| Ex. 4 | KSCN | 0.05 | 53 | 80 |
| Ex. 5 | CuCN | 0.05 | 78 | 97 |
| Ex. 6 | CuSCN | 0.05 | 70 | 95 |
| Comp. Ex. 1 | None | 0 | 24 | 54 |
| Comp. Ex. 2 | None | 0 | 5 | 69 |

EXAMPLE 7

All the reactions were carried out in a nitrogen atmosphere.

Into a 200 ml flask, 5.57 g (27 mmol) of 2-methyl-4-phenylindene, 90 mg (0.74 mmol)of copper thiocyanate and 40 ml of dehydrated diethyl ether were added. To the resulting mixture was dropwise added 18.6 ml of a hexane solution of n-butyllithium having a concentration of 1.6 mol/liter at −10° C. with stirring, and they were reacted with each other for 1 hour at −10° C.

The temperature of the reaction solution thus obtained was elevated to room temperature. Then, to the solution was added a solution of 5 ml of dehydrated diethyl ether and dimethyldichlorosilane (14.8 mmol), and they were reacted with each other for 45 minutes.

To the reaction solution was added water, and the resulting product was extracted with diethyl ether. Then, the product was purified with a silica gel column to obtain bis (2-methyl-4-phenyl-1-indenyl)dimethylsilane at a yield of 94% based on 2-methyl-4-phenyl indene.

The structure of the resulting product was confirmed by NMR.

What is claimed is:

1. A process for preparing a cyclopentadienyl group-containing silicon compound or a cyclopentadienyl group-containing germanium compound, comprising reacting:
   (i) a lithium, sodium or potassium salt of a cyclopentadiene derivative, with
   (ii) a silicon halide compound or a germanium halide compound,
   in the presence of a cyanide or a thiocyanate.

2. The process for preparing a cyclopentadienyl group-containing silicon compound or a cyclopentadienyl group-containing germanium compound as claimed in claim 1, wherein the cyanide or the thiocyanate is a copper salt.

3. The process for preparing a cyclopentadienyl group-containing silicon compound or a cyclopentadienyl group-containing germanium compound as claimed in claim 1, wherein the lithium, sodium or potassium salt of a cyclopentadiene derivative (i) is a lithium salt of a cyclopentadiene derivative.

4. The process for preparing a cyclopentadienyl group-containing silicon compound or a cyclopentadienyl group-containing germanium compound as claimed in claim 1, wherein the silicon halide compound (ii) is dihalodialkylsilane, dihalodiarylsilane or dihaloalkylarylsilane; and the germanium halide compound (ii) is dihalodialkylgermane, dihalodiarylgermane or dihaloalkylarylgermane.

* * * * *